(12) United States Patent
Kirino et al.

(10) Patent No.: US 10,844,427 B2
(45) Date of Patent: Nov. 24, 2020

(54) FOUR-LEAF CLOVER QRT-PCR: AN EFFICIENT AND CONVENIENT METHOD FOR SELECTIVE QUANTIFICATION OF MATURE TRNA

(71) Applicant: THOMAS JEFFERSON UNIVERSITY, Philadelphia, PA (US)

(72) Inventors: Yohei Kirino, Brwn Mawr, PA (US); Shozo Honda, Tokushima (JP)

(73) Assignee: Thomas Jefferson University, Philadelphia, PA (US)

( * ) Notice: Subject to any disclaimer, the term of this patent is extended or adjusted under 35 U.S.C. 154(b) by 233 days.

(21) Appl. No.: 15/570,510

(22) PCT Filed: May 2, 2016

(86) PCT No.: PCT/US2016/030404
§ 371 (c)(1),
(2) Date: Oct. 30, 2017

(87) PCT Pub. No.: WO2016/176681
PCT Pub. Date: Nov. 3, 2016

(65) Prior Publication Data
US 2019/0032111 A1    Jan. 31, 2019

Related U.S. Application Data

(60) Provisional application No. 62/155,027, filed on Apr. 30, 2015.

(51) Int. Cl.
*C12P 19/34* (2006.01)
*C12Q 1/686* (2018.01)
*C12Q 1/6851* (2018.01)

(52) U.S. Cl.
CPC ........... *C12Q 1/686* (2013.01); *C12Q 1/6851* (2013.01)

(58) Field of Classification Search
CPC ............ C12Q 1/6851; C12Q 2525/191; C12Q 2525/301; C12Q 2537/113; C12Q 1/686
See application file for complete search history.

(56) References Cited

U.S. PATENT DOCUMENTS

2014/0004520 A1   1/2014  Mohapatra
2015/0105275 A1   4/2015  Wong et al.

FOREIGN PATENT DOCUMENTS

CN    103555848 B      2/2015
WO    2012162779 A1    12/2012

OTHER PUBLICATIONS

Honda et al., "Four-leaf Clover qRT-PCR: A Convenient Method for Selective Quantification of Mature tRNA" RNA Biology. vol. 12, No. 5, pp. 501-508 (published online Apr. 1, 2015).
International Search Report dated Jul. 22, 2016 in International Patent Application No. PCT/US2016/030404.
Abbott, J.A., et al., "Transfer RNA and human disease", Frontiers in Genetics, vol. 5, Article 158, 18 pages, 2014.
Bullard, D.R., et al., "Direct comparison of nick-joining activity of the nucleic acid ligases from bacteriophage T4", Biochemical Journal, vol. 398, Pt. 1, pp. 135-144, 2006.
Chan, P.P., et al., "GtRNAdb: a database of transfer RNA genes detected in genomic sequence", Nucleic Acids Research, vol. 37, pp. D93-D97, 2009.
Chen, C., et. al., "Real-time quantification of microRNAs by stem-loop RT-PCR", Nucleic Acids Research, vol. 33, No. 20, e179, 9 pages, 2005.
Cheng, Y., et al., "Highly sensitive determination of microRNA using target-primed and branched rolling-circle amplification", Angewandte Chemie International Edition, vol. 48, No. 18, pp. 3268-3272, 2009.
Clepet, C., "RNA captor: a tool for RNA characterization", PLoS One, vol. 6, No. 4, e18445, 2011.
Dittmar, K.A., et al., "Tissue-specific differences in human transfer RNA expression", PLoS Genetics, vol. 2, No. 12, e221, pp. 2107-2115, 2006.
El Yacoubi, B., et al., "Biosynthesis and function of post-transcriptional modifications of transfer RNAs", Annals Rev Genet, vol. 46, pp. 69-95, 2012.
Gebetsberger, J., et al., "Slicing tRNAs to boost functional ncRNA diversity", RNA Biology, vol. 10, No. 12, pp. 1798-1806, 2013.
Gingold, H., et al., "A dual program for translation regulation in cellular proliferation and differentiation", Cell, vol. 158, No. 6, pp. 1281-1292, 2014.
Ho, C.K., et al., "Bacteriophage T4 RNA ligase 2 (gp24.1) exemplifies a family of RNA ligases found in all phylogenetic domains", PNAS USA, vol. 99, No. 20, pp. 12709-12714, 2002.
Ishimura, R., et al., "RNA function: Ribosome stalling induced by mutation of a CNS-specific tRNA causes neurodegeneration", Science, vol. 345, No. 6195, pp. 455-459, 2014.
Juhling, F., et al., "tRNAdb 2009: compilation of tRNA sequences and tRNA genes", Nucleic Acids Research, vol. 37, pp. D159-D162, 2009.
Kellner, S., et al., "Detection of RNA modifications", RNA Biology, vol. 7, No. 2, pp. 237-247, 2010.
Limbach, P.A., et al., "Summary: the modified nucleosides of RNA", Nucleic Acids Research, vol. 22, No. 12, pp. 2183-2196, 1994.
Lowe, T.M., et al., tRNAscan-SE: a program for improved detection of transfer RNA genes in genomic sequence:, Nucleic Acids Research, vol. 25, No. 5, pp. 955-964, 1997.
Nandakumar, J., et al., "RNA substrate specificity and structure-guided mutational analysis of bacteriophage T4 RNA ligase 2", The Journal of Biological Chemistry, vol. 279, No. 30, pp. 31337-31347, 2004.

(Continued)

*Primary Examiner* — Cynthia B Wilder
(74) *Attorney, Agent, or Firm* — Cozen O'Connor

(57) ABSTRACT

A method for quantifying individual mature tRNA species, comprising: incubating mature tRNA in a buffer to remove the amino acids from the 3' end; annealing a DNA/RNA stem-loop adapter; ligating the annealed hybrid stem-loop adapter to the mature tRNA; and amplifying and quantifying the ligation product by TaqMan qRT-PCR.

16 Claims, 11 Drawing Sheets

Specification includes a Sequence Listing.

(56) References Cited

OTHER PUBLICATIONS

Nandakumar, J., et al., "Dual mechanisms whereby a broken RNA end assists the catyalysis of its repair by T4 RNA ligase 2", The Journal of Biological Chemistry, vol. 280, No. 25, pp. 23484-23489, 2005.

Nwagwu, M., et al., "Ribonucleic acid synthesis in embryonic chick muscle, rates of synthesis and half-lives of transfer and ribosomal RNA species", J. Embryol. exp. Morph., vol. 56, pp. 253-267, 1980.

Parisien, M., et al., "Discovering RNA-protein interactome by using chemical context profiling of the RNA-protein interface", Cell Reports, vol. 3, pp. 1703-1713, 2013.

Park, K., et al., "Detection of single-base mutation in RNA using T4 RNA ligase-based nick-joining of DNAzyme-based nick-generation", Analytical Biochemistry, vol. 414, No. 2, pp. 303-305, 2011.

Pavon-Eternod, M., et al., "tRNA over-expression in breast cancer and functional consequences", Nucleic Acids Research, vol. 37, No. 21, pp. 7268-7280, 2009.

Pavon-Eternod, M., et al., "Overexpression of initiator methionine tRNA leads to global reprogramming of tRNA expression and increased proliferation in human epithelial cells", RNA, vol. 19, pp. 461-466, 2013.

Phizicky, E.M., et al., "tRNA biology charges to the front", Genes Development, vol. 24, pp. 1832-1860, 2010.

Raina, M., et al., "tRNAs as regulators of biological processes", Frontiers in Genetics, vol. 5, Article 171, 14 pages, 2014.

Shigematsu, M., et al., "Transfer RNA as a source of small functional RNA", J Mol Biol Imaging, vol. 1, No. 2, 15 pages, 2014.

Sobala, A., et al., "Transfer RNA-derived fragments: origins, processing, and functions", WIREs RNA, vol. 2, No. 6, pp. 853-862, 2011.

Suzuki, T., "A complete landscape of post-transcriptional modifications in mammalian mitochondrial tRNAs", Nucleic Acids Research, vol. 42, No. 11, pp. 7346-7357, 2014.

Telonis, A.G., et al., "Nuclear and mitochondrial tRNA-lookalikes in the human genome", Frontiers in Genetics, vol. 5, Article 344, pp. 1-11, 2014.

Zaborske, J.M., et al., "Genome-wide analysis of tRNA charging and activation of the elF2 kinase Gcn2p", The Journal of Biological Chemistry, vol. 284, pp. 25254-25267, 2009.

Zhou, Y. et al., "High levels of tRNA abundance and alteration of tRNA charging by bortezomib in multiple myeloma", Biochem Biophys Res Commun, vol. 385, No. 2, pp. 160-164, 2009.

The cellular transcriptome mainly contains 3 tRNA gene-derived RNA species.

Standard PCR will amplify all three species, and cannot selectively detect them.

tRNA harbors various post-transcriptional modifications.

Many modifications inhibit Watson–Crick base paring and thus arrest reverse-transcription.

Reverse-transcriptions for tRNAs produce severely biased results with underrepresentation of heavily-modified tRNAs.

FIG. 8

Acceptor stem region does not contain the modifications that disrupt Watson–Crick base-pairing.

The region that FL-PCR amplifies does not contain the modifications.

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Transgenic

<400> SEQUENCE: 1
tcgtagggtc cgaggtattc acgatgrgra                                    30

<210> SEQ ID NO 2
<211> LENGTH: 30
<212> TYPE: DNA
<213> ORGANISM: Artificial Sequence
<220> FEATURE:
<223> OTHER INFORMATION: Transgenic

<400> SEQUENCE: 2
tcgtagggtc cgaggtattc acgatgrgrg                                    30

<210> SEQ ID NO 3
<211> LENGTH: 29
<212> TYPE: DNA
<213> ORGANISM: Artificial Sequence
<220> FEATURE:
<223> OTHER INFORMATION: Transgenic

<400> SEQUENCE: 3
tcgtagggtc cgaggtattc acgatgrgc                                     29

<210> SEQ ID NO 4
<211> LENGTH: 29
<212> TYPE: DNA
<213> ORGANISM: Artificial Sequence
<220> FEATURE:
<223> OTHER INFORMATION: Transgenic

<400> SEQUENCE: 4
tcgtagggtc cgaggtattc acgatgrgr                                     29
```

FOUR-LEAF CLOVER QRT-PCR: AN EFFICIENT AND CONVENIENT METHOD FOR SELECTIVE QUANTIFICATION OF MATURE TRNA

FIELD OF INVENTION

The present application is generally related to methods for selective quantificaiton of mature transfer RNA.

BACKGROUND OF THE INVENTION

Transfer RNAs (tRNAs) play a central role in protein synthesis as adapter molecules and also recently appear to have a wide variety of other functions in biological processes beyond translation. Unraveling the emerging complexities of tRNA biology requires an understanding on the regulation of tRNA abundance and heterogeneity. However, accurate tRNA quantification is challenging because of the coexistence of mature tRNAs and their precursors and fragments and the presence of tRNA post-transcriptional modifications that hinder reverse transcription.

Alteration of tRNA levels because of mutations in tRNAs themselves or tRNA maturation enzymes has been reported to contribute to diseases. In addition, global expression analyses using microarray systems have revealed that tRNA abundance greatly varies among different human cells and tissues and suggested the translational regulation of mRNA expression by tRNA heterogeneity. The variations of tRNA expression are also implicated in cancer and neurodegeneration. Moreover, besides their role in translation as adapter molecules, tRNAs are now known to have a wide variety of non-canonical functions, such as in apoptosis regulation.

To unravel the emerging complexities of tRNA biology, it is imperative to accurately quantify individual tRNA species and easily analyze their expression profiles. While Northern blot analysis is a widely-used RNA detection method that requires only common molecular biology equipment, a PCR-based method could be more efficient owing to its high sensitivity and ability to distinguish variants. However, accurate tRNA quantification by standard qRT-PCR amplification of the interior sequences of the tRNA molecules is confounded by the two potential issues: specificity and the presence of tRNA modifications.

Regarding specificity, the cellular transcriptome mainly contains 3 tRNA gene-derived RNA species, precursor tRNAs (pre-tRNAs), mature tRNAs, and tRNA-derived small RNA fragments (10-12). Because these RNA species have identical sequences, standard qRT-PCR cannot be used to specifically quantify mature tRNAs because their complete sequences are present in pre-tRNAs (see FIG. 5).

Regarding tRNA modifications, tRNAs harbor the highest density of nucleoside modifications found in nature. Over 100 post-transcriptional modifications are present in tRNAs, many of which play crucial roles in tRNA folding and function such as codon recognition (16-18). Because many such modifications inhibit Watson-Crick base pairing and thus arrest reverse-transcription (19), standard qRT-PCR would produce severely biased results with underrepresentation of heavily-modified tRNAs (see FIG. 6). This modification issue is inevitable with any PCR-based technology used for the detection and quantification of RNA because there is no experimental methodology that removes all tRNA modifications.

Here we report the development of four-leaf clover qRT-PCR (FL-PCR), an efficient and convenient PCR-based method, which can specifically and accurately quantify individual mature tRNA species.

SUMMARY OF THE INVENTION

In accordance with these and other objects, a first embodiment of an invention disclosed herein is directed to a method for quantifying tRNA species comprising: removing amino acids at the 3'-end of mature aminoacylated tRNAs by deacylation; utilizing a DNA/RNA hybrid SL-adapter to specifically hybridize to the deacylated mature tRNA wherein the SL-adapter contains 5'-P and 3'-OH termini, and identical loop sequences with stem-loop R printer for microRNA quantification; the two 3' terminal nucleotides of the adapter are RNA, whereas the remaining nucleotides are DNA; and wherein the 3'-terminal nucleotide is designed to be complementary to a discriminator base of tRNA; following hybridization, T4 RNA Ligase 2 (Rnl2) ligates nicks between the SL-adapter and mature tRNA to produce a "four leaf clover" structure; wherein the ligation product is amplified and quantified using TaqMan qRT-PCR with forward and reverse primers derived from the T- and D-loop of targeted tRNAs, and a TaqMan probe targeting the SL-adapter.

FL-PCR process will provide a much-needed simple method for analyzing tRNA abundance and heterogeneity, the factors that may play an important regulatory role in translation and other multiple biological processes. FL-PCR includes three steps. First, amino acids at the 3'-ends of mature aminoacylated tRNAs are removed by incubating total RNA in high pH buffer (deacylation treatment). Second, a DNA/RNA hybrid SL-adapter is specifically hybridized and ligated to mature tRNAs by Rnl2 nick ligations, generating tRNA-adapter ligation products with a "four-leaf clover" secondary structure. Last, the ligation product is amplified and quantified by TaqMan qRT-PCR. FL-PCR circumvents the two problems previously hindering quantification of mature tRNA: specificity and the presence of tRNA modifications.

Regarding specificity, the SL-adapter was designed to selectively recognize mature tRNAs within total RNAs (see FIG. 7). Of the 3 tRNA species included in total RNA (pre-tRNAs, mature tRNAs and tRNA fragments), only mature tRNAs contain both mature 5'- and 3'-ends, and the 3'-teminal nucleotides of the SL-adapter are designed to be complementary only to the mature ends. Hence, mature tRNAs are the only tRNA gene-derived RNA species that are specifically quantified by FL-PCR. Regarding modifications, FL-PCR limits the main amplified regions of mature tRNA to the unmodified acceptor stem; therefore FL-PCR is not expected to be influenced by the presence of tRNA modifications (see FIG. 8).

A further embodiment is directed to a method for quantifying individual mature tRNA species, comprising: incubating mature tRNA in a buffer to remove the amino acids from the 3' end; annealing a DNA/RNA hybrid stem-loop adapter; ligating the annealed hybrid stem-loop adapter to the mature tRNA; and amplifying and quantifying the ligation product by TaqMan qRT-PCR.

A further embodiment is directed to a method for quantifying mature tRNA comprising: deacylating the 3'ends of mature aminoacylated tRNA; hybridizing a Stem-Loop adapter to the acylated mature tRNA; ligating the nicks between the SL adapter and mature tRNA to produce a four-leaf-clover structure; and amplifying and quantifying the ligation product.

A further embodiment is directed to a kit for quantifying mature tRNA comprising: a deacylation buffer; a DNR/RNA-hybrid stem loop adapter; an annealing buffer; a ligating buffer comprising T4-RNA ligase 2; and a reverse transcriptase primer; wherein the kit contents can be utilized to quantify mature tRNA according to instructions for using such components for quantification of the mature tRNA.

Additional features and embodiments will be apparent to one of ordinary skill in the art upon consideration of the following detailed description of preferred embodiments and descriptions of the best mode of carrying out the invention.

BRIEF DESCRIPTION OF THE DRAWINGS

FIG. 8 depicts that FL-PCR is not influenced by the presence of tRNA modifications.

DETAILED DESCRIPTION OF THE PREFERRED EMBODIMENTS

Figure 1:
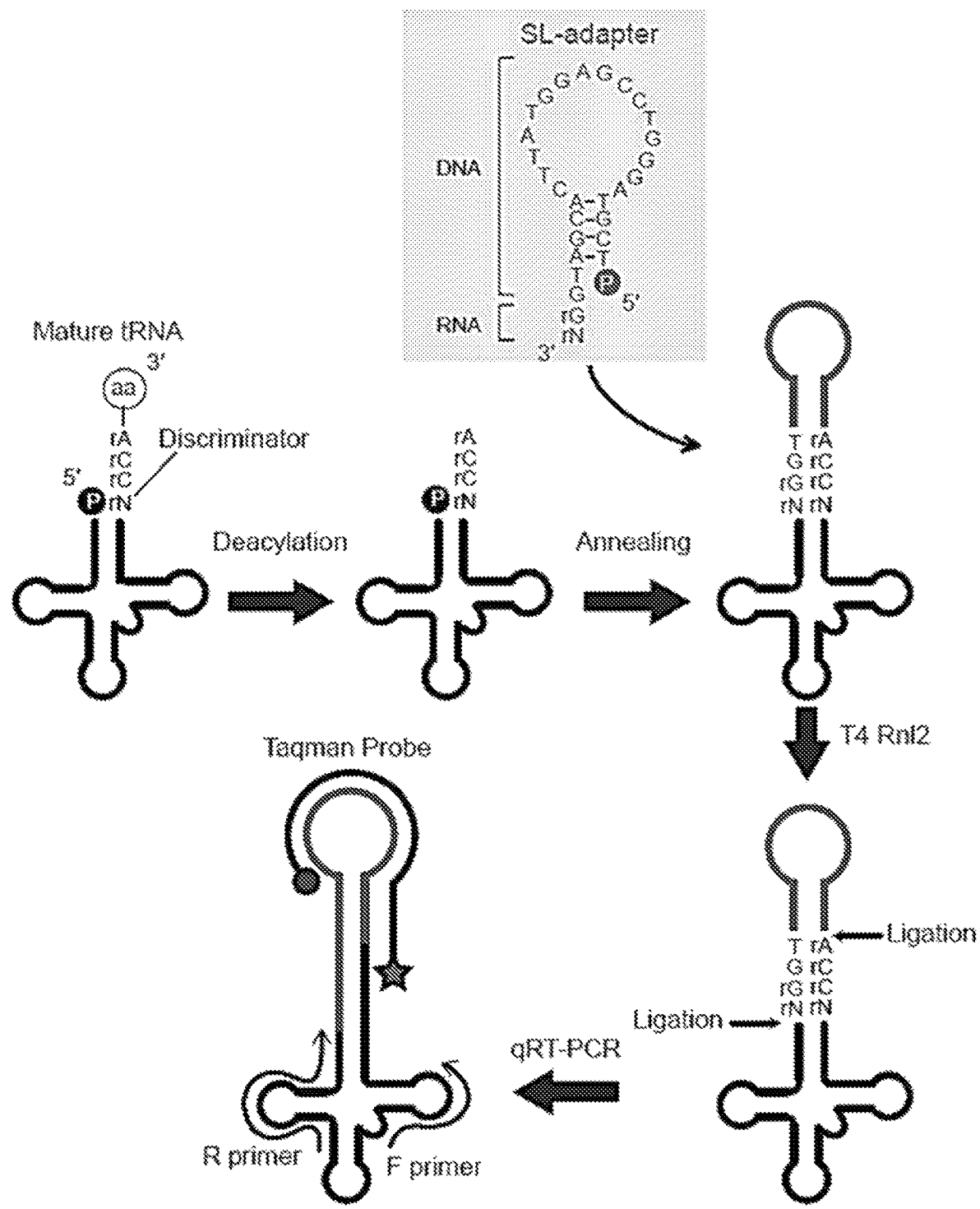
FIG. 1 is a schematic representation of mature tRNA quantification by FL-PCR.

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

Transfer RNAs (tRNAs) are 70-90-nucleotide (nt) noncoding RNA molecules that fold into a cloverleaf secondary structure and L-shaped tertiary structure. tRNAs are universally expressed in all living organisms and play a central role in gene expression as an adapter molecule that translates codons in mRNA into amino acids in protein. The human nuclear genome encodes over 500 tRNA genes (1) along with numerous tRNA-lookalikes resembling nuclear and mitochondrial tRNAs (2). Active transcription from multiple sites of the genome, along with high stability (3), place tRNAs among the most abundant RNA molecules in the cellular transcriptome. Because of their abundance and well-defined house-keeping role in translation, the enthusiasm to understand the quantitative aspects of tRNAs has not been very high. However, alteration of tRNA levels because of mutations in tRNAs themselves or tRNA maturation enzymes has been reported to contribute to diseases (4). In addition, global expression analyses using microarray system have revealed that tRNA abundance greatly varies among different human cells and tissues and suggested the translational regulation of mRNA expression by tRNA heterogeneity (5-7). The variations of tRNA expression are also implicated in cancer and neurodegeneration (8, 9). Moreover, besides their role in translation as adapter molecules, tRNAs are now known to have a wide variety of non-canonical functions, such as in apoptosis regulation (10, 11). tRNAs have further been reported to serve as a source of small functional RNAs (12-14). Numerous tRNA-interacting proteins have recently been proposed (15), indicating the scope of tRNA biological functions may be far beyond that previously assumed.

The four-leaf clover qRT-PCR (FL-PCR), is an efficient and convenient PCR-based method, which can specifically and accurately quantify individual mature tRNA species. FIG. 1 depicts a schematic representation of mature tRNA quantification by FL-PCR. Amino acids at the 3'-ends of mature aminoacylated tRNAs are removed by deacylation treatment. A DNA/RNA hybrid SL-adapter is then specifically hybridized to the deacylated mature tRNAs. The SL-adapter contains 5'-P and 3'-OH termini, and identical loop sequences with stem-loop RT primer for microRNA quantification [22]. The two 3'-terminal nucleotides of the adapter are RNA, whereas all other nucleotides are composed of DNA. The 3'-terminal nucleotide is designed to be complementary to a discriminator base of tRNA. Following hybridization, Rnl2 ligates the nicks between the SL-adapter and mature tRNA to produce a "four-leaf-clover" structure. Finally, the ligation product is amplified and quantified using TaqMan qRT-PCR with forward and reverse primers derived from the T- and D-loop of targeted tRNAs, respectively, and a TaqMan probe targeting the SL-adapter.

The FL-PCR procedure includes a nick-ligation step catalyzed by Rnl2. Rnl2 was originally identified in the bacteriophage T4 (20) and catalyzes RNA ligation at a 3'-OH/5'-P nick in a double-stranded RNA (dsRNA) or an RNA-DNA hybrid (21-23). Because of this peculiar ligation activity toward double-stranded nucleotides, Rnl2 is an attractive tool for adapter ligation in cDNA preparation (24) and detection of microRNAs (25) and SNPs (26). In our method, Rnl2 specifically ligates a stem-loop adapter (SL-adapter) to mature tRNAs, but not to pre-tRNAs or tRNA fragments, to generate a four-leaf clover-like structure. Subsequently, TaqMan qRT-PCR amplifies the unmodified region of the tRNA-adapter ligation product, which is not influenced by tRNA modification. FL-PCR thus resolves the issues with standard qRT-PCR and provides an efficient and convenient method for selective and accurate quantification of mature tRNA pools.

In FL-PCR, Rnl2 specifically ligates a stem-loop adapter (SL-adapter) to mature tRNAs but not to precursor tRNAs or tRNA fragments, resulting in high specificity toward mature tRNAs. Subsequent TaqMan qRT-PCR amplifies only unmodified regions of the tRNA-adapter ligation products; thus, FL-PCR accurately quantifies mature tRNA pools without being influenced by tRNA modifications. FL-PCR also has broad applicability for the quantification of different tRNAs in different cell types. FL-PCR thus provides a much-needed simple method for analyzing tRNA abundance and heterogeneity, the factors that may play an important regulator role in translation and other biological processes.

Accordingly, the FL-PCR method circumvents the two problems previously hindering quantification of mature tRNA: specificity and the presence of tRNA modifications. Regarding specificity, the SL-adapter was designed to selectively recognize mature tRNAs within total RNAs. Of the three tRNA species included in total RNA (pre-tRNAs, mature tRNAs, and tRNA fragments), only mature tRNAs contain both mature 5'- and 3'-ends in the secondary structure, these mature ends protrude as a four-nucleotide sequence consisting of the trinucleotide, 5'-CCA-3', and the discriminator base preceding them. The 3'-terminal nucleotide of the SL-adapter and subsequent 5'-TGG-3' sequence are designed to be complementary to the four protruding nucleotides of mature tRNAs, enabling the adapter to exclusively hybridize to mature tRNAs but not to pre-tRNAs or tRNA fragments (see FIG. 7). Hence, mature tRNAs are the only tRNA gene-derived RNA species that are specifically quantified by FL-PCR.

FL-PCR also circumvents the issue of tRNA modifications that hinder reverse transcription. Although the positions and species of modifications in tRNAs are not comprehensively identified in full detail, research on tRNA biology suggests that tRNA modifications occur non-randomly at conserved positions, such as positions 34 and 37 in the anticodon-loop, and positions 9 and 10 between acceptor- and D-stems. To our knowledge, it has not been previously shown that there are modifications in the acceptor stem of mature tRNAs that disrupt Watson-Crick base-pairing. FL-PCR was designed to limit the main amplified regions of mature tRNA to the unmodified acceptor stem; therefore FL-PCR is not expected to be influenced by the presence of tRNA modifications (see FIG. 8).

Therefore the FL-PCR process will provide a much-needed simple method for analyzing tRNA abundance and heterogeneity, the factors that may play an important regulatory role in translation and other multiple biological processes. Accordingly, FL-PCR is a method for determining abundance and heterogeneity of tRNA.

Materials and Methods

Human mature tRNA sequences Variant sequences of human cytoplasmic (cyto) tRNA$^{AspGUC}$, cyto tRNA$^{ValAAC/CAC}$ and cyto tRNA$^{LysCUU}$ were identified using the tRNA-scan-SE program (1, 27). The tRNA sequences were sorted by mismatches and aligned using DNADynamo software (BlueTractor Software).

Cell Lines

HeLa and BT-474 cell lines were cultured in Dulbecco's modified Eagle's medium (DMEM; Life Technologies) containing 10% fetal bovine serum (FBS). ZR-75-1, T-47D, HCC1937, BT-549, DU145, PC-3, and LNCaP-FGC cell lines were cultured in RMPI1640 medium (Life Technologies) containing 10% FBS. The BT-20 cell line was cultured in minimum essential medium (MEM; Life Technologies) containing 10% FBS.

Total RNA Isolation and Deacylation Treatment

Total RNA from cell lines was extracted using a product for isolating RNA sold under the trademark TRISURE™ (Bioline) according to the manufacturer's protocol. Total RNAs were incubated at 37.degree. C. for 40 min in 20 mM Tris-HCl (pH 9.0) to remove the amino acids from the mature tRNAs (deacylation treatment), followed by ethanol precipitation.

Annealing and Ligation of Stem-Loop Adaptors to Mature tRNAs

The DNA/RNA-hybrid SL-adapters shown in Table 1 were synthesized by Integrated DNA Technologies. Each adapter (20 pmol) was incubated with 100 ng of the deacylated total RNA in 9 μL mixture at 90° C. for 3 min. After adding 1 μL of 10× annealing buffer containing 50 mM Tris-HCl (pH 8.0), 5 mM EDTA, and 100 mM MgCl$_2$, the total 10 μL mixture was annealed by incubation at 37° C. for 20 min. To ligate the annealed adapter to mature tRNAs, 10 μL of the 1× reaction buffer containing 1 unit of T4 RNA ligase 2 (New England Biolabs) was added to the mixture. The entire mixture (20 μL) was incubated at 37° C. for 1 h, followed by overnight incubation at 4° C. This overnight incubation increased the ligation efficiency by more than 3 times (data not shown).

Explanation of the Stem-Loop Adapter (SL-Adapter)

TABLE 1

Sequences of adaptors and primers for FL-PCR

| Name | Sequence (5'-3') |
| --- | --- |
| SL-adaptor-A (SEQ ID NO: 1) | /5Phos/TCGTAGGGTCCGAGGTATTACGATGrGrA |
| SL-adaptor-G (SEQ ID NO: 2) | /5Phos/TCGTAGGGTCCGAGGTATTACGATGrGrG |
| SL-adaptor-C (SEQ ID NO: 3) | /5Phos/TCGTAGGGTCCGAGGTATTACGATGrGrC |
| SL-adaptor-U (SEQ ID NO: 4) | /5Phos/TCGTAGGGTCCGAGGTATTACGATGrGrU |

The SL-adapter in Table 1, are 28 nucleotides composing of DNA except for the last two 3'-terminal nucleotides that have been designed to be RNA (indicated as rA, rG, rC, or rU in Table 1). The adapter contains 5'-P and 3'-OH termini, a four bp-stem region (the bold letters in Table 1 form the stem), a loop-region, and four nucleotide protruding 3'-terminal sequences (5'-TGrGrN-3'; rN is either rA, rG, rC, or rU). The protruding sequences speciеically recognize 3'-terminal protruding sequences (5'-NCCA-3') of mature tRNAs. N in the 5'-NCCA-3' is discriminator base which can be A, G, C, or U depending on tRNA species. Because SL-adapter should match mature tRNA sequences, SL-adaptor-A, SL-adaptor-G, SL-adaptor-C, and SL-adaptor-U will be used to quantify the tRNAs containing discriminator base U, C, G, A, respectively.

TaqMan Quantitative RT-PCR for Mature tRNAs

Ligated RNA (1 μL) was incubated with 1 pmol of specific RT primer (Table 1) and 5 nmol of dNTPs in 7 μL mixture at 90° C. for 2 min and then placed on ice. Reverse transcription was subsequently performed by adding Super-Script™ III Reverse Transcriptase and its reaction buffer (Life Technologies) to create a 10 μL mixture and incubating for 30 min at 55° C. (for cyto tRNA$^{AspGUC}$, cyto tRNA$^{ValAAC/CAC}$, and mt tRNA$^{GluUUC}$) or at 42° C. (for cyto tRNA$^{LysCUU}$ and mt tRNA$^{AlaUGC}$). The resultant cDNA solution was diluted by 1:5, and 1.5 μL of this solution was added to the Real-time PCR mixture containing 5 μL of 2× Premix Ex Taq reaction solution (Clontech Lab), 400 nM TaqMan probe; Integrated DNA Technologies), and specific forward and reverse primers (2 pmol each) derived from targeted mature tRNA sequences (10 μL in total) (Table 1). A StepOne Plus Real-time PCR machine (Applied Biosystems) was used; the reaction mixture was incubated at 95° C. for 20 s, followed by 40 cycles of 95° C. for 1 s and 65° C. (for cyto tRNA$^{LysCUU}$) 60° C. (for cyto tRNA$^{AspGUC}$, cyto tRNA$^{ValAAC/CAC}$, and mt tRNA$^{AlaUGC}$), or 55° C. (mt tRNA$^{GluUUC}$) for 20 s. All reactions were run in triplicate and the threshold cycles (Ct) were determined. When required, 5S rRNA expression was quantified for use as an internal control using SsoFast EvaGreen Supermix (BioRad) and appropriate primers. The amplified cDNA was developed by 3% Metaphor gel (LONZA) or 10% native PAGE.

Northern Blot Analysis

Briefly, the total RNA (100 ng for cyto tRNA$^{AspGUC}$ or 4 μg for mt tRNA$^{GluUUC}$) was resolved by 12% PAGE containing 7M urea, transferred to Hybond N$^+$ membranes (GE Healthcare) and hybridized to 5'-end labeled antisense probes. The visualization and quantification were performed with storage phosphor autoradiography using Typhoon-9400 and ImageQuant ver. 5.2 (GE Healthcare).

Results and Discussion

Four-leaf clover qRT-PCR (FL-PCR) design scheme and rationale. We designed and tested FL-PCR for selective amplification of mature tRNAs. The method includes three steps (FIG. 1). First, amino acids at the 3'-ends of mature aminoacylated tRNAs are removed by incubating total RNA in high pH buffer (deacylation treatment). Second, a DNA/RNA hybrid stem-loop adapter (SL-adapter) is specifically hybridized and ligated to mature tRNAs by Rnl2 nick ligations, generating tRNA-adapter ligation products with a "four-clover-leaf" secondary structure. Last, the ligation product is amplified and quantified by TaqMan qRT-PCR. FL-PCR circumvents the two problems previously hindering quantification of mature tRNA: specificity and the presence of tRNA modifications.

Regarding specificity, the SL-adapter, which harbors loop sequences identical to those of the stem-loop RT primer for microRNA quantification (28), was designed to selectively recognize mature tRNAs within total RNAs. Of the 3 tRNA species included in total RNA (pre-tRNAs, mature tRNAs and tRNA fragments), only mature tRNAs contain both mature 5'- and 3'-ends. In the secondary structure, these mature ends protrude as a four-nucleotide sequence consisting of the trinucleotide, 5'-CCA-3', and the discriminator base preceding them. The 3'-teminal nucleotide of the SL-adapter and subsequent 5'-TGG-3' sequence are designed to be complementary to the four protruding nucleotides of mature tRNAs, enabling the adapter to exclusively hybridize to mature tRNAs but not to pre-tRNAs or tRNA fragments (FIG. 1). The hybridization unites the tRNA acceptor stem and SL-adapter stem to form long, double-stranded DNA/RNA hybrids containing two nicks ("adapter-3'/5'-tRNA" and "tRNA-3'/5'-adapter"). Because both the mature tRNA and SL-adapter contain 5'-P and 3'-OH, both nicks form 3'-OH/5'-P, a perfect substrate for Rnl2 ligase. The SL-adapter nucleotides are composed of DNA except for the last two 3'-terminal nucleotides that have been designed to be RNA (FIG. 1). This design converts the nicks in "adapter-3'/5'-tRNA" and "tRNA-3'/5'-adapter" to "RNA-3'/5'-RNA" and "RNA-3'/5'-DNA", both of which are efficient substrates for Rnl2 ligation (21-23).

The subsequent TaqMan qRT-PCR was designed to be completely dependent on the Rnl2 double-nick ligation to exclusively amplify "four-clover-leaf" tRNA-adapter ligation products. This was achieved by deriving the TaqMan probe and RT-PCR primers from the SL-adapter and tRNA, respectively. Hence, mature tRNAs are the only tRNA gene-derived RNA species that are specifically quantified by FL-PCR.

FL-PCR also circumvents the issue of tRNA modifications that hinder reverse transcription. Although the positions and species of modifications in tRNAs are not comprehensively identified in full detail, research on tRNA biology suggests that tRNA modifications occur non-randomly at conserved positions, such as positions 34 and 37 in the anticodon-loop, and position 9 and 10 between acceptor- and D-stems (16-18, 29). To our knowledge, it has not been previously shown that there are modifications in the acceptor stem of mature tRNAs that disrupt Watson-Crick base-pairing. In the TaqMan qRT-PCR of FL-PCR, the forward and reverse primers were designed to be derived from the T- and D-arms of targeted mature tRNA, respectively, and the amplified cDNAs are quantified using the TaqMan probe targeting the SL-adapter (FIG. 1). This design limits the main amplified regions of mature tRNA to the unmodified acceptor stem; therefore FL-PCR is not expected to be influenced by the presence of tRNA modifications.

Selective Amplification and Quantification of Human Cyto Mature tRNA$^{AspGUC}$ by FL-PCR FIG. 2 depicts FL-PCR amplification and quantification of mature cyto tRNA$^{AspGUC}$ in HeLa cells, therefore confirming the efficacy of FL-PCR according to this process. (A) Secondary structure of SL-adapter and targeted human cyto tRNA$^{AspGUC}$-V1. The regions from which the primers and TaqMan probe were derived are shown. (B) Left: SL-adapter sequences with a 4 bp or 10 bp stem used in FL-PCR. Right: Metaphor gel electrophoresis of the amplified cDNA resulting from FL-PCR for cyto tRNA$^{AspGUC}$-V1 using HeLa total RNA. The expected band size from the adapter with 4 bp or 10 bp stem is 98 or 104 bp, respectively; a specific band was only observed from the 4 bp stem adapter, indicating that only 4 bp stem adaptor works for the FL_PCR. (C) Left: Metaphor gel electrophoresis of cDNA amplified by FL-PCR with or without Rnl2 ligation reaction and substrate total RNA. HeLa total RNA was used for the cyto tRNA$^{AspGUC}$-V1 detection. Only the reaction from total RNA treated with Rnl2 ligation showed a clear amplified band, indicating that the method successfully amplifies ligation products. (D) Proportional correlation of HeLa total RNA input (50, 100, 200, and 400 ng) to the cycle threshold (Ct) obtained by FL-PCR targeting cyto tRNA$^{AspGUC}$-V1. Thus, the quantifications showed clear linearity between the log of sample input and Ct value, indicating that the FL-PCR method is capable of quantifying tRNA amounts.

Figure 2A:
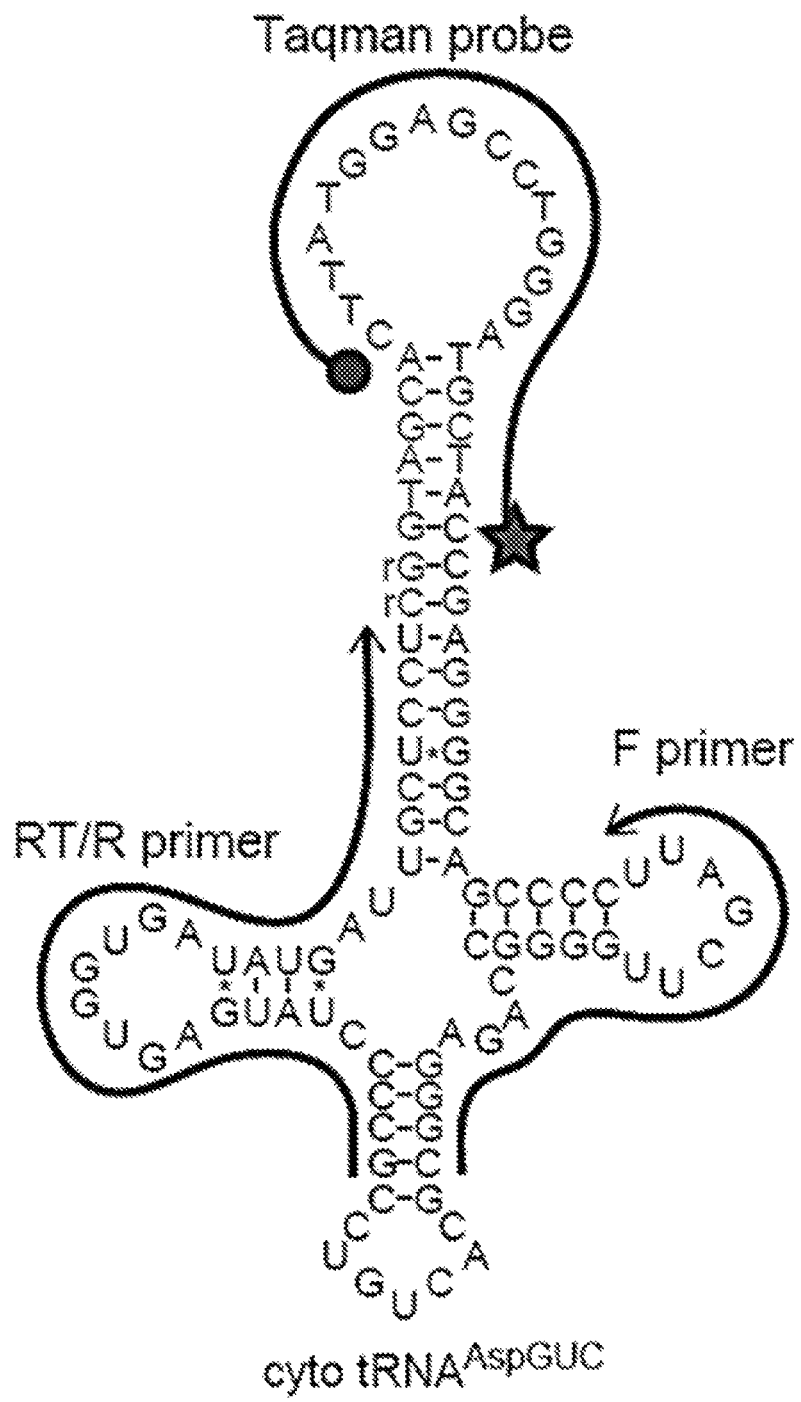
FIGS. 2A-2D depicts FL-PCR amplification and quantification of mature tRNA in HeLa cells.
Figure 2B:
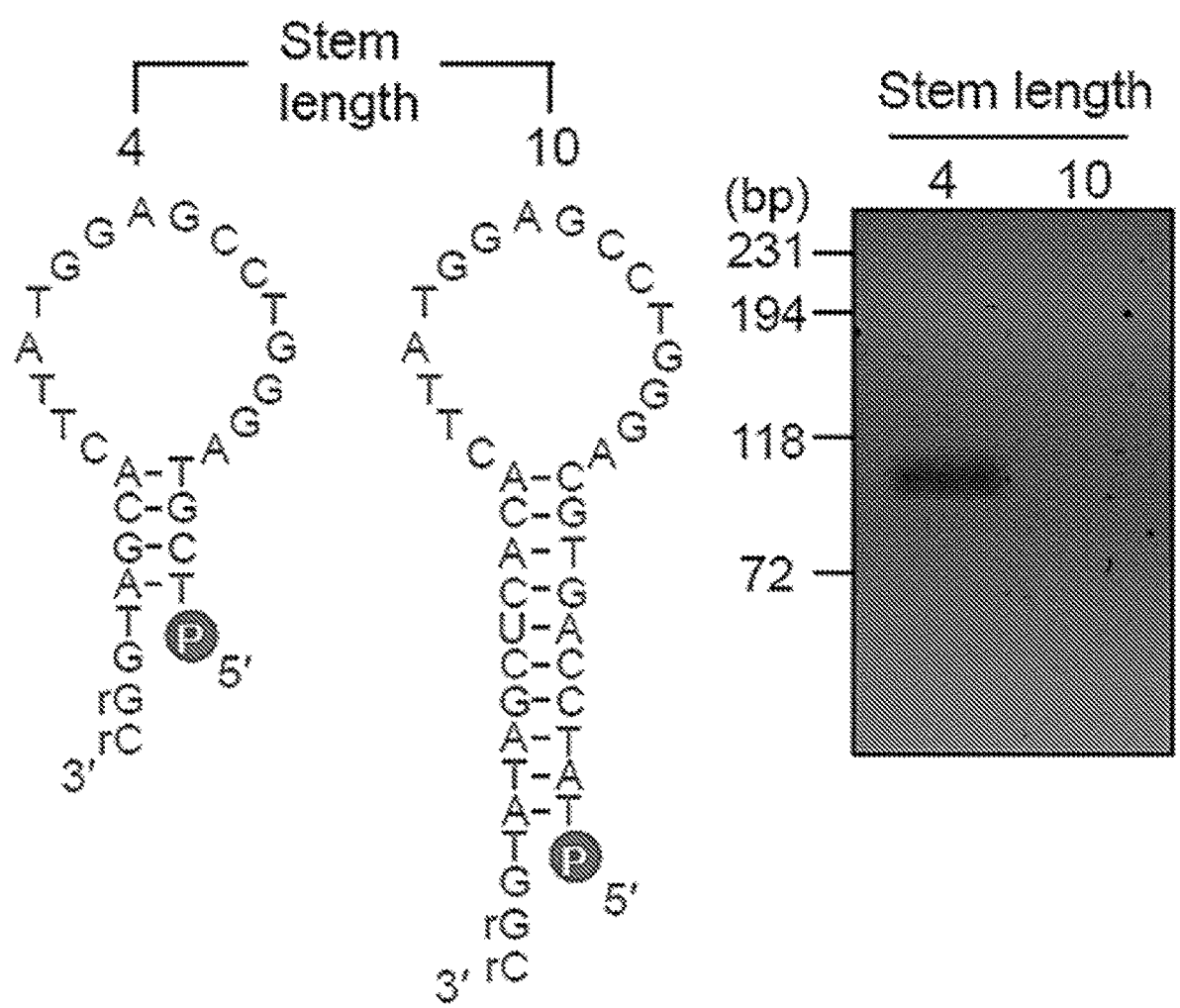
Figure 2C:
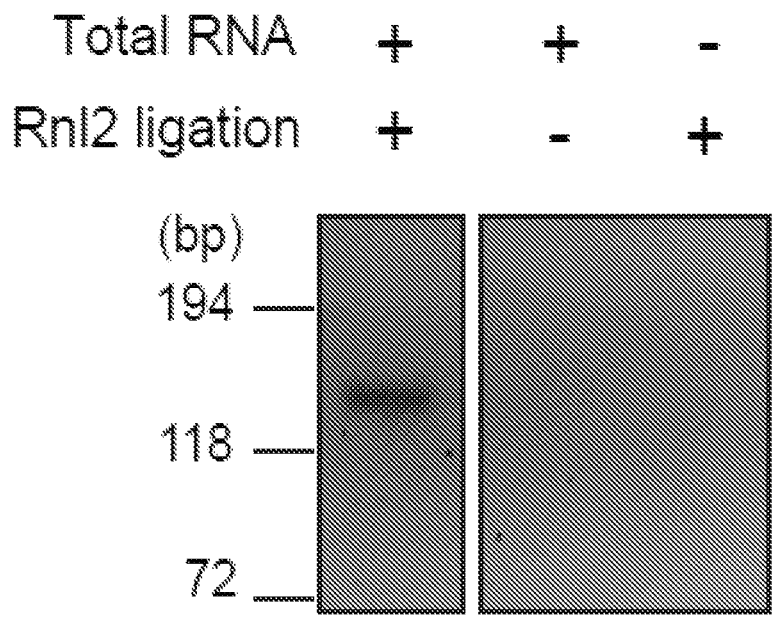

The FL-PCR scheme was first evaluated by targeting human cytoplasmic (cyto) tRNA$^{AspGUC}$-V1, the most abundantly encoded variant of cyto tRNA$^{AspGUC}$ in the human genome (FIG. 2A). Because the discriminator base of the tRNA is G, the SL-adapter containing a 3'-terminal C was used for detection. We observed FL-PCR-amplification of endogenous mature tRNA$^{AspGUC}$-V1 from HeLa total RNA as a single amplified band (FIG. 2B). As expected, the sequences of the cDNA band were determined to be derived from the amplified region of the tRNA-adapter ligation product.

Figure 2D:
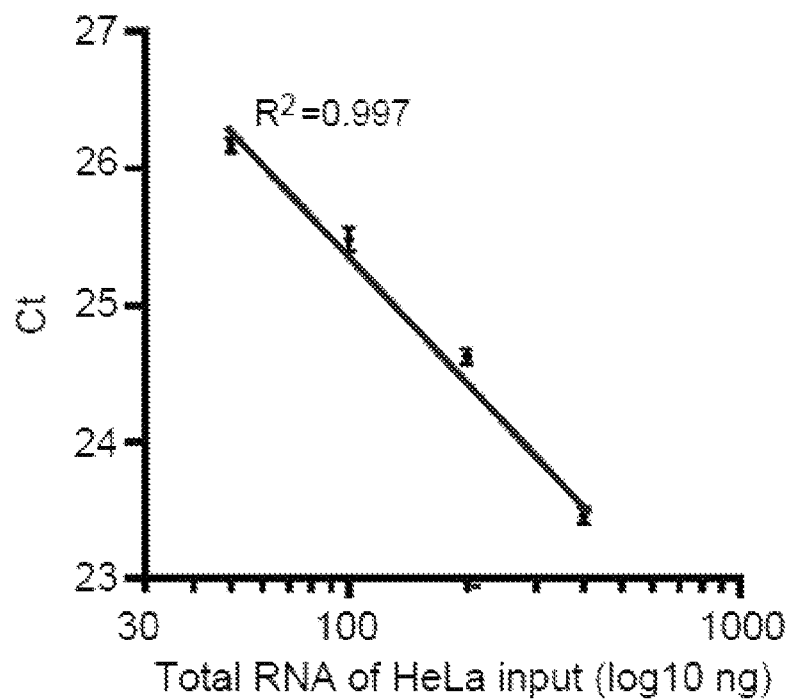

In the process of determining the most effective SL-adapter construct, the stem-length of the adapter was a critical factor. While the adapter containing a stem of 4 bp length succeeded in amplifying the tRNA, the adapter with a 10 bp stem did not (FIG. 2B), most likely because the secondary structure of the tRNA-adapter ligation product would contain 21 bp stems and thus become too rigid for qRT-PCR. The stem-loop adapter with a 4 bp stem was used in the experiments that followed. FL-PCR without Rnl2 ligation procedure failed to give a detectable signal (FIG. 2C), further confirming that FL-PCR selectively amplifies tRNA-adapter ligation products. To examine the quantification ability, FL-PCR was applied for different amounts of synthetic cyto tRNA$^{AspGUC}$ and HeLa total RNA (FIG. 2D). The quantifications showed clear linearity between the log of sample input and Ct value, indicating that the FL-PCR method is capable of quantifying relative amounts of synthetic tRNA and of endogenous tRNA in total RNA.

FL-PCR Quantification of Various Mature tRNAs in Human Cell Lines

FIG. 3 depicts FL-PCR amplification of various human mature tRNAs, showing the feasibility of using FL-PCR to quantify other tRNAs. (A) Secondary structure of human cyto tRNA$^{ValAAC/CAC}$, cyto tRNA$^{LysCUU}$, mt tRNA$^{GluUUC}$, and mt tRNA$^{AlaUGC}$. Based on the discriminator base species, the SL-adapter containing 3'-terminal U was used for the detection of cyto tRNA$^{ValAAC/CAC}$, mt tRNA$^{GluUUC}$, and mt tRNA$^{AlaUGC}$, whereas tRNA$^{LysCUU}$ was amplified by the adapter containing 3'-terminal C. The regions from which primers were derived are indicated. (B) FL-PCR using HeLa total RNA generated specific bands of amplified cDNAs developed by native PAGE. The expected band size of amplified cDNAs is 82, 69, 93, or 92 bp for cyto tRNA$^{ValAAC/CAC}$, cyto tRNA$^{LysCUU}$, mt tRNA$^{GluUUC}$, or mt tRNA$^{AlaUGC}$, respectively. All four FL-PCR reactions using HeLa total RNA targeting respective tRNAs generated single amplified bands of cDNAs, indicating the broad applicability of FL-PCR for the quantification of various mature tRNAs.

FIG. 4 depicts quantification of mature tRNAs in human cell lines. (A) FL-PCR quantifications of cyto tRNA$^{AspGUC}$ and mt tRNA$^{GluUUC}$ in human breast cancer cell lines (ZR-75-1, T-47D, BT-474, HCC1937, BT-20, and BT-549), prostate cancer cell lines (DU145, PC-3, and LNCaP-FGC), and HeLa cells. The tRNA abundances were normalized by 5S rRNA levels, and the abundance in BT-474 cells was defined as 1. Each data set represents the average of three independent experiments, with bars showing the SD. (B) Northern blot quantifications of cyto tRNA$^{AspGUC}$ and mt tRNA$^{GluUUC}$ in human cell lines. The tRNA abundances were normalized by 5S rRNA levels, and the abundance in BT-474 cells was defined as 1. Each data set represents the average of three independent experiments, with bars showing the SD. Therefore, overall expression patterns determined by FL-PCR were quite consistent with those determined by Northern blots, indicating that FL-PCR is as accurate as Northern blot.

Figure 3A:
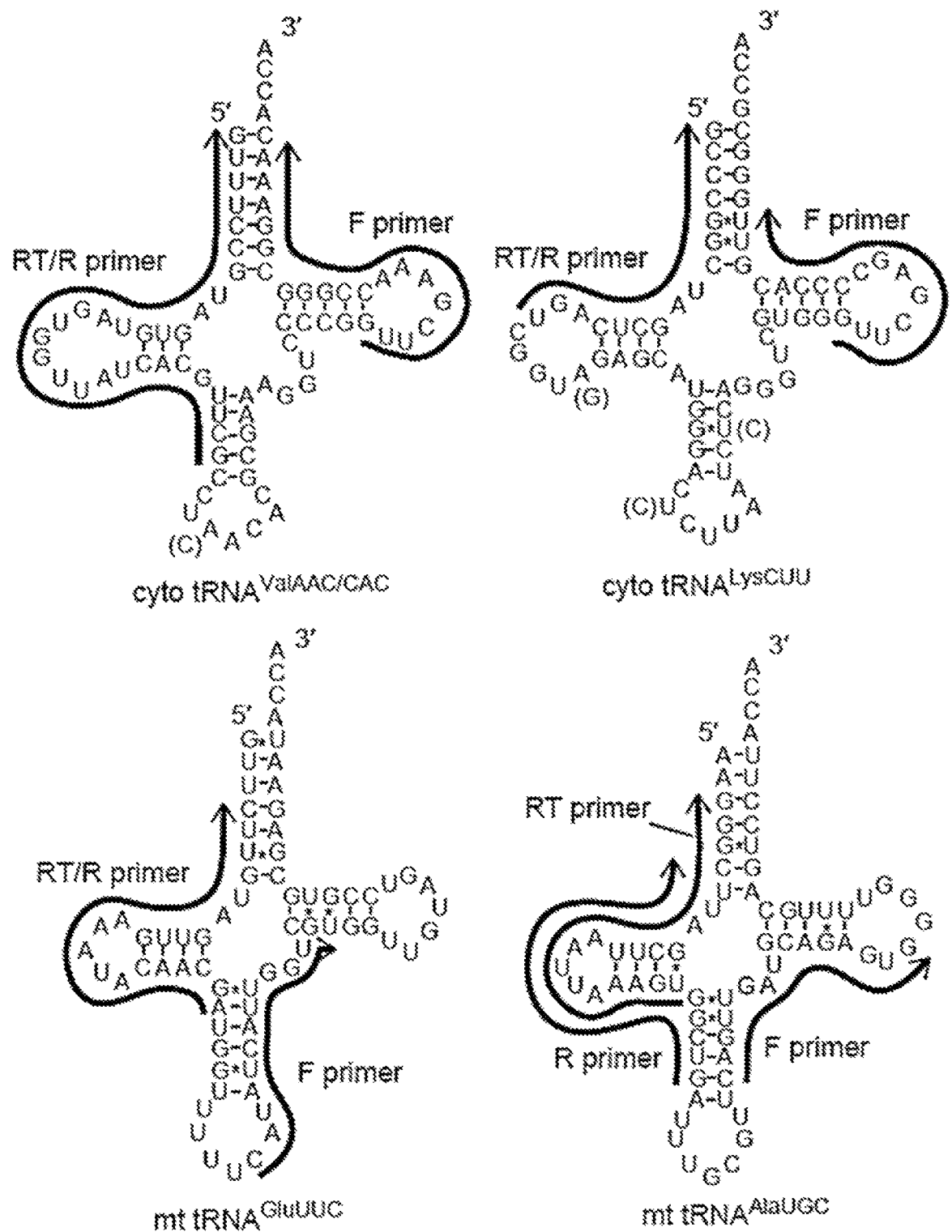
FIGS. 3A-3B depicts FL-PCR amplification of various human mature tRNAs.
Figure 3B:
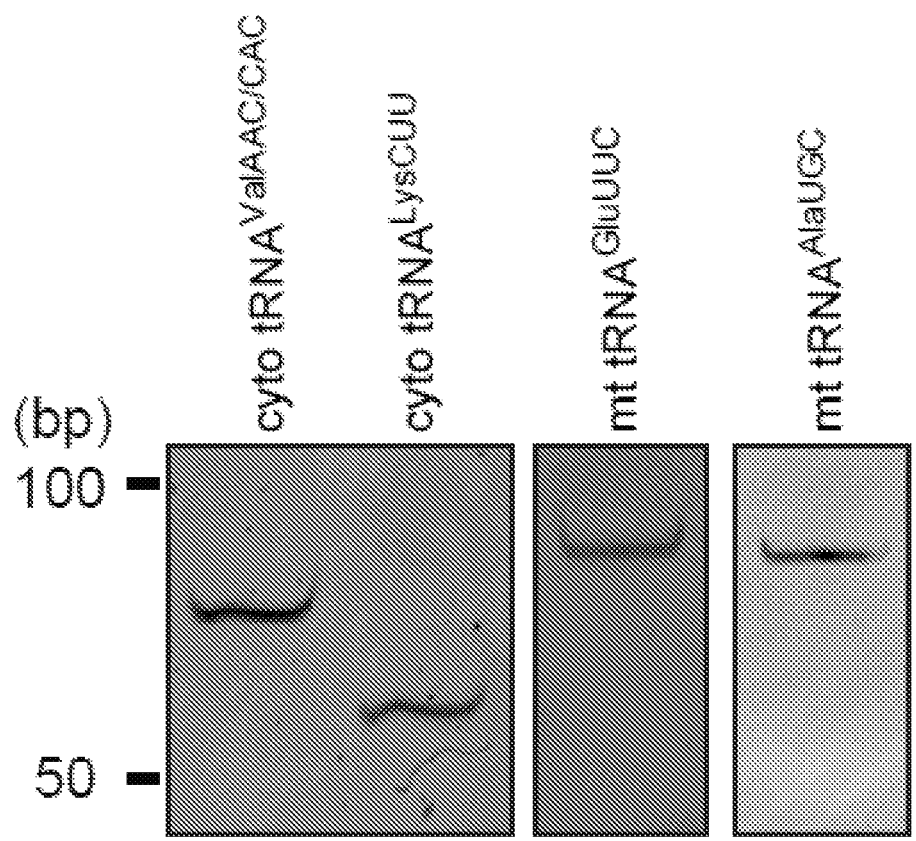

To examine the feasibility of using FL-PCR to quantify other tRNAs, we further targeted human cyto tRNA$^{ValAAC}$-V1 and -V3/tRNA$^{ValCAC}$-V1 and -V2, cyto tRNA$^{LysCUU}$-V1, -V2, -V3, and -V4, mitochondrial (mt) tRNA$^{GluUUC}$, and mt tRNA$^{AlaUGC}$ (FIG. 3A). Based on the discriminator base species, the SL-adapter containing 3'-terminal U was used for the detection of cyto tRNA$^{ValAAC/CAC}$, mt tRNA$^{GluUUC}$, and mt tRNA$^{AlaUGC}$, whereas tRNA$^{LysCUU}$ was amplified by the adapter containing 3'-terminal C. As shown in FIG. 3B, all four FL-PCR reactions using HeLa total RNA targeting respective tRNAs generated single amplified bands of cDNAs whose sequences were confirmed to be derived from the amplified regions of the respective tRNA-adapter ligation products. These results indicate the broad applicability of FL-PCR for the amplification and quantification of various mature tRNAs.

Figure 4A:
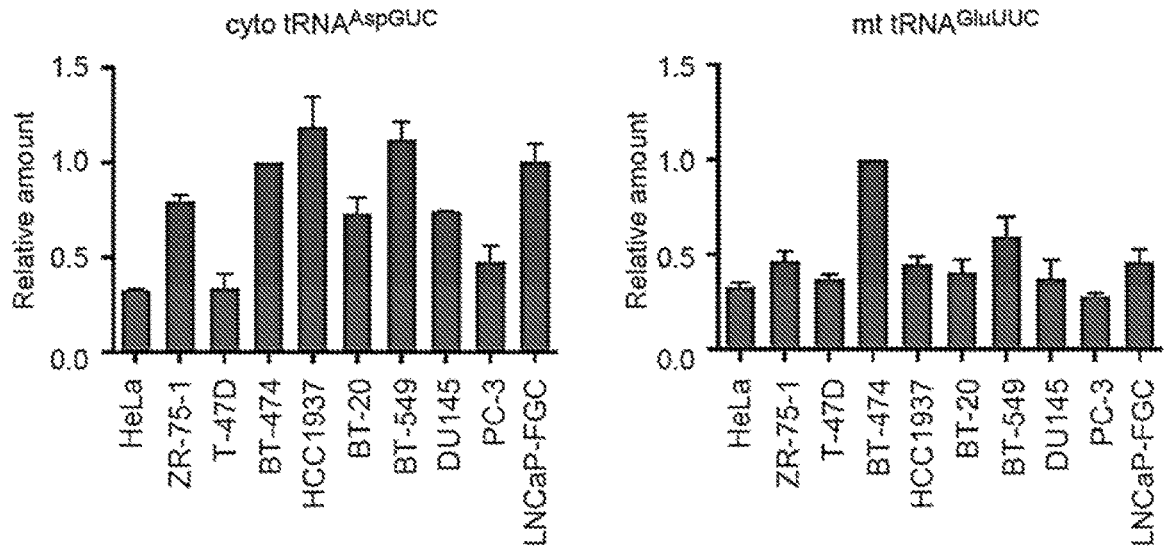
FIGS. 4A-4B depicts FL-PCR amplification and quantification of mature tRNAs in various human cell lines.
Figure 4B:
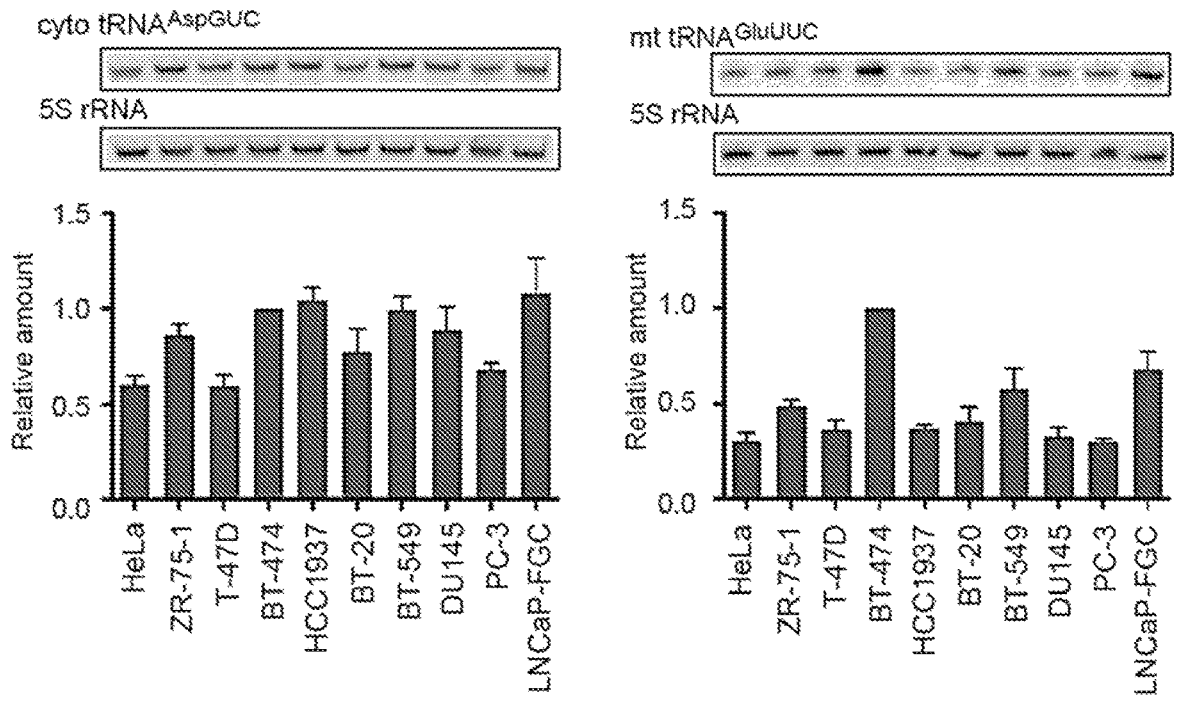

Using FL-PCR, the expression profiles of cyto tRNA$^{AspGUC}$ and mt tRNA$^{GluUUC}$ were determined in identical amounts of total RNA from 10 different human cell lines (FIG. 4A). Each mature tRNA showed distinctive expression patterns in different cell lines. We further quantified the two mature tRNAs by Northern blot analysis, a current standard technique to quantify mature tRNAs. As shown in FIG. 4B, overall expression patterns of the both examined tRNAs determined by FL-PCR were quite consistent with those determined by Northern blots. These results indicate the broad applicability and accuracy of FL-PCR for the examination of heterogeneities in tRNA expression profiles in various different cell types.

Figure 5:
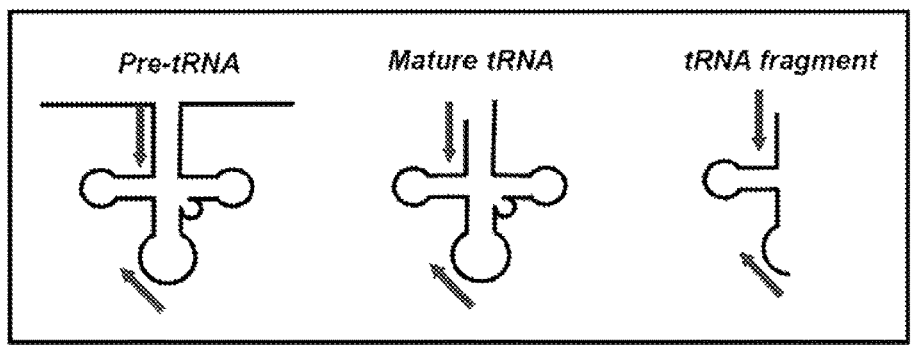
FIG. 5 depicts that standard PCR cannot selectively detect pre-tRNA, mature tRNA or its fragment.

FIG. 5 identifies an issue in standard qRT-PCR for tRNA quantification. Indeed, as depicted, standard PCR cannot selectively detect pre-tRNA, mature tRNA or its fragment because standard PCR will amplify all three species, and cannot selectively detect between them. The cells mainly contain three tRNA-derived RNA species, precursor tRNAs (pre-tRNAs), mature tRNAs, and tRNA-derived small RNA fragments. Because these RNA species have identical sequences, standard qRT-PCR amplifying interior sequences cannot distinguish between them.

Figure 6:
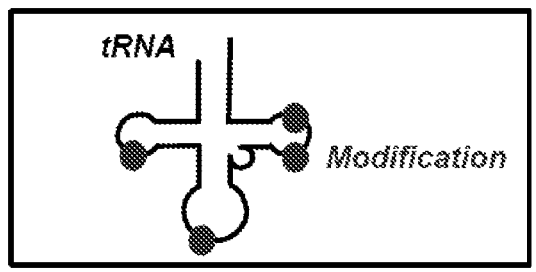
FIG. 6 depicts that standard PCR cannot precisely quantify tRNAs because of the presence of tRNA modifications.
Figure 6:
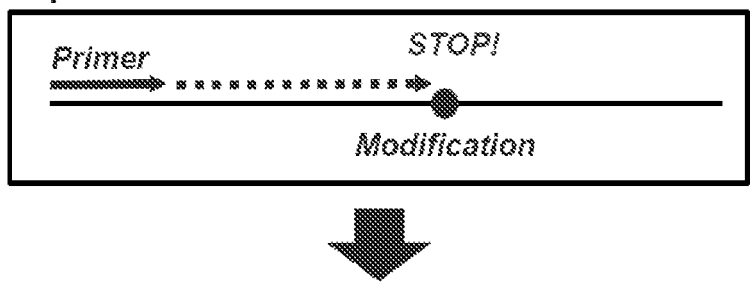

FIG. 6 depicts a second problem with standard qRT-PCR for tRNA quantification. Indeed, tRNAs harbor many post-transcriptional modifications, many of which arrest reverse-transcription. Therefore, standard qRT-PCR would produce severely biased results with underrepresentation of heavily-modified tRNAs. that standard PCR cannot precisely quantify tRNAs because of the presence of tRNA modifications.

Figure 7:
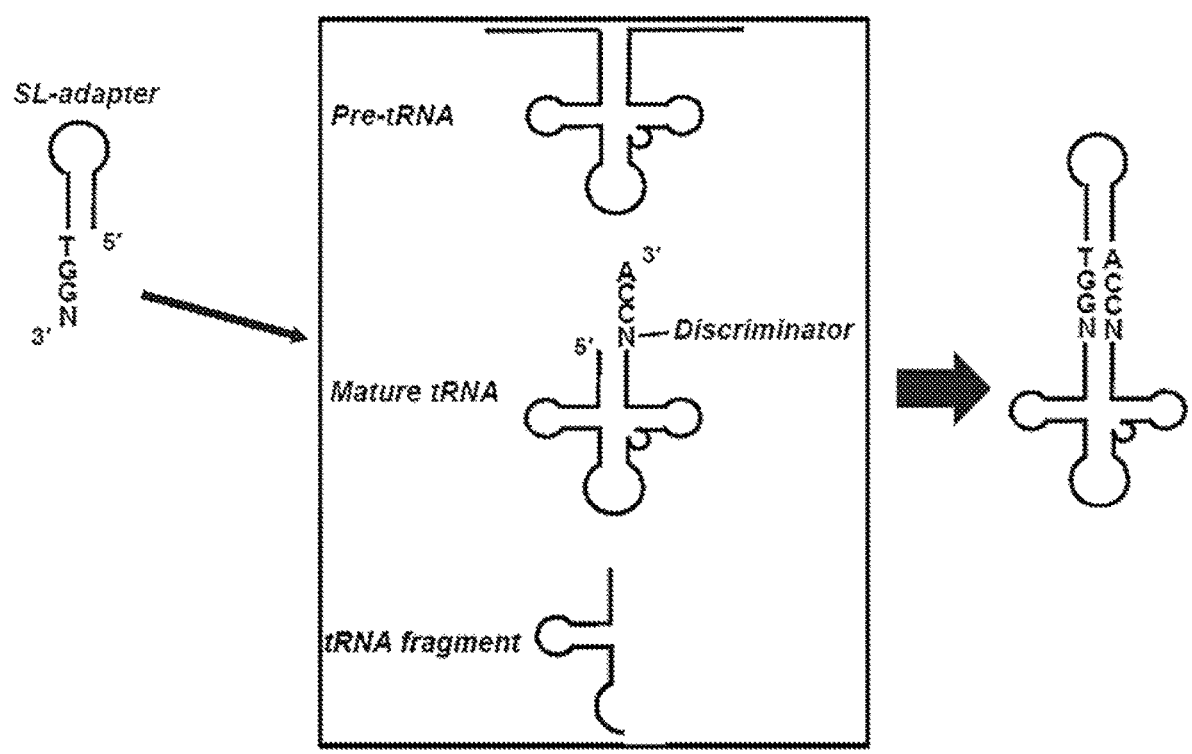
FIG. 7 depicts that in FL-PCR, the SL-adapter specifically recognizes mature tRNAs within total RNAs.

FIG. 7 depicts that FL-PCR solves the issue in FIG. 5, as in FL-PCR, the SL-adapter specifically recognizes mature tRNAs within total RNAs. Accordingly, use of FL-PCR enables specific quantification of mature tRNAs (not their precursors and fragments). Note the discriminator 4 base tag on the 3' end of the mature tRNA that specifically binds with the SL-adapter.

FIG. 8 depicts that FL-PCR is not influenced by the presence of tRNA modifications because the acceptor stem region does not contain the modifications that disrupt Watson-Crick base pairing. Therefore, FL-PCR provides a second advantage to solve the second issue, as described in FIG. 6. The design scheme of FL-PCR limits the amplified regions of mature tRNA to the unmodified acceptor stem; therefore FL-PCR is not expected to be influenced by the presence of tRNA modifications.

In conclusion, FL-PCR is developed as an efficient and convenient method for selective amplification and quantification of mature tRNAs that is not influenced by the presence of tRNA modifications. The method has high specificity for mature tRNAs, quantitative capability to estimate relative expression levels, and broad applicability for the quantification of different tRNAs in different cell types. As our view of tRNA function is constantly being expanded, FL-PCR will provide a much-needed simple method for analyzing tRNA abundance and heterogeneity, the factors that may play an important regulatory role in translation and other multiple biological processes.

Therefore, it is envisioned that the FL-PCR process can be effectively utilized in methods for amplification and quantification of mature tRNA. Such methods are advantageously utilized with kits that contain the reagents and components described herein, and instructions providing a detail of the methods to perform the FL-PCR process to amplify and quantify mature tRNAs.

An embodiment of a particular kit comprises all the reagents necessary to perform the FL-PCR process. This includes the reagents to remove the amino acids at the 3'-ends of mature aminoacylated tRNAs and instructions for incubating total RNA in high pH buffer (deacylation treatment). Second, the kit includes each of the four DNA/RNA hybrid SL-adapter (e.g. SEQ ID NO: 1-4) and the reagents to specifically hybridized and ligate to mature tRNAs by Rnl2 nick ligations so as to generate tRNA-adapter ligation products with a "four-leaf clover" secondary structure. The kit can optionally include the reagents and instructions for TaqMan qRT-PCR. Preferably, the kit contents are provided such that each reagent is individually packaged in an aliquot or regent bottle. Certain components are routine materials used in a laboratory setting and instructions to formulate such routine materials may be included in place of, or in addition to an aliquot or pre-made reagent components.

In other embodiments, the kit comprises a deacylation buffer; a set of four DNR/RNA-hybrid stem loop adapters (SEQ ID NO: 1-4); an annealing buffer; a ligating buffer comprising T4-RNA ligase 2; and a reverse transcriptase primer; wherein the kit contents can be utilized to quantify mature tRNA according to instructions for using such components for quantification of the mature tRNA.

REFERENCES

1. Chan, P. P. and Lowe, T. M. (2009) GtRNAdb: a database of transfer RNA genes detected in genomic sequence. Nucleic Acids Res, 37, D93-97.
2. Telonis, A. G., Loher, P., Kirino, Y. and Rigoutsos, I. (2014) Nuclear and mitochondrial tRNA-lookalikes in the human genome. Front Genet, 1-11.
3. Nwagwu, M. and Nana, M. (1980) Ribonucleic acid synthesis in embryonic chick muscle, rates of synthesis and half-lives of transfer and ribosomal RNA species. J Embryol Exp Morphol, 56, 253-267.
4. Abbott, J. A., Francklyn, C. S. and Robey-Bond, S. M. (2014) Transfer RNA and human disease. Front Genet, 5, 158.
5. Dittmar, K. A., Goodenbour, J. M. and Pan, T. (2006) Tissue-specific differences in human transfer RNA expression. PLoS Genet, 2, e221.
6. Pavon-Eternod, M., Gomes, S., Geslain, R., Dai, Q., Rosner, M. R. and Pan, T. (2009) tRNA over-expression in breast cancer and functional consequences. Nucleic Acids Res, 37, 7268-7280.
7. Gingold, H., Tehler, D., Christoffersen, N. R., Nielsen, M. M., Asmar, F., Kooistra, S. M., Christophersen, N. S., Christensen, L. L., Borre, M., Sorensen, K. D. et al. (2014) A dual program for translation regulation in cellular proliferation and differentiation. Cell, 158, 1281-1292.
8. Pavon-Eternod, M., Gomes, S., Rosner, M. R. and Pan, T. (2013) Overexpression of initiator methionine tRNA leads to global reprogramming of tRNA expression and increased proliferation in human epithelial cells. RNA, 19, 461-466.
9. Ishimura, R., Nagy, G., Dotu, I., Zhou, H., Yang, X. L., Schimmel, P., Senju, S., Nishimura, Y., Chuang, J. H. and Ackerman, S. L. (2014) RNA function. Ribosome stalling induced by mutation of a CNS-specific tRNA causes neurodegeneration. Science, 345, 455-459.
10. Raina, M. and Ibba, M. (2014) tRNAs as regulators of biological processes. Front Genet, 5, 171.
11. Phizicky, E. M. and Hopper, A. K. (2010) tRNA biology charges to the front. Genes Dev, 24, 1832-1860.
12. Shigematsu, M., Honda, S. and Kirino, Y. (2014) Transfer RNA as a source of small functional RNA. J Mol Biol Mol Imag, in press.
13. Gebetsberger, J. and Polacek, N. (2013) Slicing tRNAs to boost functional ncRNA diversity. RNA Biol, 10, 1798-1806.
14. Sobala, A. and Hutvagner, G. (2011) Transfer RNA-derived fragments: origins, processing, and functions. Wiley Interdiscip Rev RNA, 2, 853-862.
15. Parisien, M., Wang, X., Perdrizet, G., 2nd, Lamphear, C., Fierke, C. A., Maheshwari, K. C., Wilde, M. J., Sosnick, T. R. and Pan, T. (2013) Discovering RNA-protein interactome by using chemical context profiling of the RNA-protein interface. Cell Rep, 3, 1703-1713.
16. Juhling, F., Morl, M., Hartmann, R. K., Sprinzl, M., Stadler, P. F. and Putz, J. (2009) tRNAdb 2009: compilation of tRNA sequences and tRNA genes. Nucleic Acids Res, 37, D159-162.
17. Limbach, P. A., Crain, P. F. and McCloskey, J. A. (1994) Summary: the modified nucleosides of RNA. Nucleic Acids Res, 22, 2183-2196.
18. El Yacoubi, B., Bailly, M. and de Crecy-Lagard, V. (2012) Biosynthesis and function of posttranscriptional modifications of transfer RNAs. Annu Rev Genet, 46, 69-95.
19. Kellner, S., Burhenne, J. and Helm, M. (2010) Detection of RNA modifications. RNA Biol, 7, 237-247.
20. Ho, C. K. and Shuman, S. (2002) Bacteriophage T4 RNA ligase 2 (gp24.1) exemplifies a family of RNA ligases found in all phylogenetic domains. Proc Natl Acad Sci USA, 99, 12709-12714.
21. Nandakumar, J., Ho, C. K., Lima, C. D. and Shuman, S. (2004) RNA substrate specificity and structure-guided mutational analysis of bacteriophage T4 RNA ligase 2. J Biol Chem, 279, 31337-31347.
22. Nandakumar, J. and Shuman, S. (2005) Dual mechanisms whereby a broken RNA end assists the catalysis of its repair by T4 RNA ligase 2. J Biol Chem, 280, 23484-23489.
23. Bullard, D. R. and Bowater, R. P. (2006) Direct comparison of nick-joining activity of the nucleic acid ligases from bacteriophage T4. Biochem J, 398,135-144.
24. Clepet, C. (2011) RNA captor: a tool for RNA characterization. PLoS One, 6, e18445.
25. Cheng, Y., Zhang, X., Li, Z., Jiao, X., Wang, Y. and Zhang, Y. (2009) Highly sensitive determination of microRNA using target-primed and branched rolling-circle amplification. Angew Chem Int Ed Engl, 48, 3268-3272.
26. Park, K., Choi, B. R., Kim, Y. S., Shin, S., Hah, S. S., Jung, W., Oh, S. and Kim, D. E. (2011) Detection of single-base mutation in RNA using T4 RNA ligase-based nick-joining or DNAzyme-based nick-generation. Anal Biochem, 414, 303-305.
27. Lowe, T. M. and Eddy, S. R. (1997) tRNAscan-SE: a program for improved detection of transfer RNA genes in genomic sequence. Nucleic Acids Res, 25,955-964.

28. Chen, C., Ridzon, D. A., Broomer, A. J., Zhou, Z., Lee, D. H., Nguyen, J. T., Barbisin, M., Xu, N. L., Mahuvakar, V. R., Andersen, M. R. et al. (2005) Real-time quantification of microRNAs by stem-loop RT-PCR. Nucleic Acids Res, 33, e179.

29. Suzuki, T. (2014) A complete landscape of post-transcriptional modifications in mammalian mitochondrial tRNAs. Nucleic Acids Res, 42, 7346-7357.

30. Zaborske, J. M., Narasimhan, J., Jiang, L., Wek, S. A., Dittmar, K. A., Freimoser, F., Pan, T. and Wek, R. C. (2009) Genome-wide analysis of tRNA charging and activation of the eIF2 kinase Gcn2p. J Biol Chem, 284, 25254-25267.

31. Zhou, Y., Goodenbour, J. M., Godley, L. A., Wickrema, A. and Pan, T. (2009) High levels of tRNA abundance and alteration of tRNA charging by bortezomib in multiple myeloma. Biochem Biophys Res Commun, 385, 160-164.

What is claimed is:

1. A method for quantifying individual mature tRNA species, comprising:
   a. incubating mature tRNA in a buffer to remove the amino acids from the 3' end;
   b. annealing a DNA/RNA hybrid stem-loop adapter to mature tRNA;
   c. ligating the annealed stem-loop adapter to the mature tRNA; and
   d. amplifying and quantifying the ligation product by TaqMan qRT-PCR.

2. The method of claim 1, wherein the incubation step is performed at 37° C. in a pH 9.0 Tris-HCl buffer for about 40 min.

3. The method of claim 1, wherein the hybrid stem-loop adapter is selected from the group consisting of SEQ ID NO: 1-4.

4. The method of claim 1, wherein the annealing step further comprises annealing the stem-loop adapter with the incubated mature tRNA at 90° C. for 3 minutes.

5. The method of claim 1, wherein the annealing step further comprises an annealing buffer added to the stem-loop adapter, wherein said annealing step comprises incubation at 37° C. for 20 minutes.

6. The method of claim 1, wherein the ligation step comprises a reaction buffer of T4-RNA Ligase 2.

7. The method of claim 6, wherein the ligation step is incubated at 37° C. for one hour.

8. The method of claim 7, further comprising a further incubation overnight at 4° C.

9. A method for quantifying mature tRNA comprising:
   a. deacylating the 3' ends of mature aminoacylated tRNA;
   b. hybridizing a stem-loop adapter to the deacylated mature tRNA;
   c. ligating one or more nicks between the stem-loop adapter and mature tRNA to produce a four-leaf-clover structure; and
   d. amplifying and quantifying the ligation product.

10. The method of claim 9, wherein the deacylation step is performed at 37° C. in a pH 9.0 Tris-HCl buffer for about 40 min.

11. The method of claim 9, wherein the hybrid Stem-loop adapter is selected from the group consisting of SEQ ID NO: 1-4.

12. The method of claim 9, wherein after the hybridizing step comprises annealing the hybrid stem-loop adapter with the incubated mature tRNA at 90° C. for 3 minutes.

13. The method of claim 12, wherein the hybridizing step further comprises an annealing buffer added to the hybrid stem-loop adapter, wherein said annealing step comprises incubation at 37° C. for 20 minutes.

14. The method of claim 9, wherein the ligation step comprises a reaction buffer of T4-RNA Ligase 2.

15. The method of claim 14, wherein the ligation step is incubated at 37° C. for one hour.

16. The method of claim 15, further comprising a further incubation overnight at 4° C.

* * * * *